United States Patent [19]

Sunderland et al.

[11] Patent Number: 5,236,004
[45] Date of Patent: Aug. 17, 1993

[54] AMBULATORY SUPPORT DEVICE FOR A FLUID DELIVERY SYSTEM

[75] Inventors: Richard A. Sunderland, St. Charles, Mo.; Frederick C. Deno, Brownville; John A. Lane, Watertown, both of N.Y.

[73] Assignee: Sherwood Medical Company, St. Louis, Mo.

[21] Appl. No.: 819,300

[22] Filed: Jan. 9, 1992

Related U.S. Application Data

[63] Continuation-in-part of Ser. No. 679,886, Apr. 3, 1991, Pat. No. 5,170,817.

[51] Int. Cl.⁵ .............................................. F16L 3/00
[52] U.S. Cl. ............................... 137/343; 137/355.28; 128/DIG. 12; 604/151; 417/360
[58] Field of Search ................. 417/360; 604/151; 248/346; 128/DIG. 12; 137/565, 355.16, 355.28, 343

[56] References Cited

U.S. PATENT DOCUMENTS

| | | | |
|---|---|---|---|
| 3,228,474 | 1/1966 | Huthsing, Jr. | 169/31 |
| 3,880,188 | 4/1975 | Oakley, Jr. et al. | 137/577 |
| 3,972,649 | 8/1976 | Jutte | 417/53 |
| 4,207,889 | 6/1980 | Oloff et al. | 128/213 |
| 4,311,050 | 1/1982 | Bessman | 73/427 |
| 4,397,639 | 8/1983 | Eschweiler et al. | 604/153 |
| 4,416,595 | 11/1983 | Cromie | 417/476 |
| 4,479,761 | 10/1984 | Bilstad et al. | 417/395 |
| 4,496,351 | 1/1985 | Hillel et al. | 604/250 |
| 4,507,112 | 3/1985 | Hillel et al. | 604/65 |
| 4,513,796 | 4/1985 | Miller et al. | 141/83 |
| 4,545,783 | 10/1985 | Vaughan | 604/259 |
| 4,657,486 | 4/1987 | Stempfle et al. | 417/12 |
| 4,688,595 | 8/1987 | Srebnik et al. | 137/343 |
| 4,699,613 | 10/1987 | Donawick et al. | 604/80 |
| 4,720,636 | 1/1988 | Benner, Jr. | 250/573 |
| 4,722,734 | 2/1988 | Kolln | 604/151 |
| 4,756,706 | 7/1988 | Kerns et al. | 604/66 |
| 4,798,580 | 1/1989 | DeMeo et al. | 604/30 |
| 4,832,584 | 5/1989 | Nassif | 417/477 |
| 4,909,786 | 3/1990 | Gijselhart et al. | 604/65 |
| 4,919,649 | 4/1990 | Timothy et al. | 604/65 |
| 5,011,378 | 4/1991 | Brown et al. | 417/360 |
| 5,057,081 | 10/1991 | Sunderland | 604/153 |

FOREIGN PATENT DOCUMENTS

| | | |
|---|---|---|
| 3606930 | 9/1987 | Fed. Rep. of Germany . |
| 2162241 | 7/1973 | France . |
| 8691413 | 8/1985 | PCT Int'l Appl. . |
| 9007947 | 7/1990 | PCT Int'l Appl. . |

OTHER PUBLICATIONS

Fresenius AG, Frenta-System for Continuous Tube Feeding, Instruction for Use, Date Unknown, 13 Pages.
Ross Laboratories, Introducing Flexiflo Companion Enteral Nutrition Pump, Feb. 1988, 2 Pages.
Ross Laboratories, Flexiflo Companion Enteral Nutrition Pump Operating Manual, Aug. 1987, pp. 1-16.

Primary Examiner—A. Michael Chambers
Attorney, Agent, or Firm—Andrew J. Beck; Montgomery W. Smith; Gene B. Kartchner

[57] ABSTRACT

The present invention relates to a support device for use with a fluid delivery system which includes a fluid delivery set and an infusion pump. The support device allows simple attachment of various types of fluid delivery sets and infusion pumps thereto and is adapted for use with bed ridden patients in a traditional manner, or for ambulatory patient use. The support device includes a compartment for securely holding an infusion pump and a separate compartment for securely holding a fluid container of the fluid delivery set. The device further includes an elongate channel into which the tubing of the fluid delivery set can be inserted and subsequently protected from kinking or inadvertent occlusion, and is adapted for use with rigid bottle, flexible bag, burette, spike sets, or other standard types of fluid delivery sets. The device may be used on an infusion pole in a standard manner, placed on a horizontal surface such as a table, or enclosed in a carrying case for ambulatory use.

17 Claims, 19 Drawing Sheets

AMBULATORY SUPPORT DEVICE FOR A FLUID DELIVERY SYSTEM

This application is a continuation-in-part of co-pending U.S. patent application Ser. No. 679,886 filed Apr. 3, 1991 titled "Support Device for a Fluid Delivery System and Case Therefore" now U.S. Pat. No. 5,170,817 issued Dec. 15, 1992.

BACKGROUND OF THE INVENTION

1. Field of the Invention

This invention relates generally to a fluid delivery system. More specifically, the present invention relates to a support device used as a part of an ambulatory fluid delivery system for supporting and protecting the pump, fluid container, tubing, drip chamber, etc. of the system during use.

2. Description of the Prior Art

It is common for patient's having certain medical problems to require periodic premeasured infusions of fluid, such as medicaments or nutrients, into their bodies. Examples of such patients are those who may require nutrients to be delivered directly into their digestive tract periodically over long periods of time, or cancer patients who require exacting amounts of medication to be delivered intravenously at precise intervals.

In the past, such patients required hospitalization for the time necessary to infuse the nutrients or medicaments, in order to allow medical personnel to perform the infusions at the proper time and in the proper amounts. Such a procedure was extremely time consuming to the patient and also the hospital personnel, and included the potential of human error in calculation of infusion dosages and injection time intervals.

An improvement on the above procedure has been to employ a programmable pump to insure that the patient receives the proper infusion dosage at the proper time period, thus relieving medical personnel from constant monitoring of the patient, and from worrying about infusion amounts and time tables. Although the programmable pump greatly relieves medical personnel of time consuming care to the patient, the patient nevertheless remains bound to the hospital bed during the prolonged infusion periods.

A further improvement has been to develop an infusion system which can not only automatically infuse preset volumes of fluid into the patient on a predetermined time table, but also allow the patient to be ambulatory. U.S. Pat. No. 4,657,486 to Stemple et al., U.S. Pat. No. 4,397,639 to Eschweiler et al., and U.S. Pat. No. 4,416,595 to Cromie, are exemplary of portable infusion systems of this type. Each discloses a portable infusion device which is automatically operable at selected time intervals to inject accurate amounts of fluid medication into a patient's body, and is also sufficiently compact and portable to allow the patient to be ambulatory during the infusion procedure.

U.S. Pat. No. 4,688,595 to Srebnik et al. is also exemplary of fluid delivery systems of this type. Srebnik discloses a delivery system which includes an integrally molded platform to which elements of the delivery system, i.e., the pump, the fluid container, etc. can be connected. The platform allows the entire fluid delivery system to be transportable as a unit and makes it possible for the patient to move about without the inconvenience of transporting a more cumbersome apparatus such as a prior art type infusion system which was commonly affixed to a pole mounted on wheels.

Although there have been improvements in portable fluid delivery systems in the past, there nevertheless remain several inadequacies. First, the prior art fluid infusion systems generally include a programmable pump, and a fluid delivery set comprising a fluid container, tubing, pinch clamp, drip chamber, etc., all connected as an integral unit. The container of the fluid delivery sets may be a flexible bag, a rigid glass or plastic bottle or a burette. Sometimes these standard fluid delivery sets (intended for non-ambulatory use) include rather long tubular extensions to allow the fluid container to be placed on an infusion pole while the distal end of the tube can be attached to a bed ridden or non-ambulatory patient. These sets are generally ill suited for placement in a portable device such as that described by Srebnik et al., because the portable system requires significantly shorter tubing extension to properly operate. The excess tubing becomes cumbersome and inhibitive of proper operation of the system and often becomes occluded or pinched off during ambulatory use. Often, such prior art ambulatory systems have required a unique "non-standard" tubing design in order to allow the fluid delivery set to be properly attached to the pump. Since the "non-standard" ambulatory sets (such as shown by Stemple et al.) are generally unsuitable for use on standard non-ambulatory systems, it has been necessary for hospitals and other medical facilities to stock "non-standard" fluid delivery sets for use in ambulatory-type systems, and standard sets for all other uses.

OBJECTS AND SUMMARY OF THE INVENTION

Briefly, and in general terms, the present invention provides for ambulatory use of a "standard" fluid delivery set, of a fluid delivery system, while at the same time provides for reliable prevention of kinking or occlusion of excess tubing and other inadvertent damage to the system.

It is therefore an object of the present invention to provide a portable fluid delivery system which is designed to accommodate standard fluid delivery sets commonly intended for non-ambulatory use.

It is another object of the present invention to provide a fluid delivery system which is designed to avoid occlusions or damage to the tubing of the fluid delivery sets.

It is another object of the present invention to provide a support device for a fluid delivery system which will allow use of standard fluid delivery sets (designed for non-ambulatory use) thereon and which will protect and avoid occlusion of any excess tubing therein.

It is another object of the present invention to provide a support device which is readily adaptable for use with soft bag, blow molded bottle, glass bottle, or burette-type fluid containers of fluid delivery sets.

It is a further object of the present invention to provide a support device which allows for the pump of the fluid delivery system to be readily attached or detached therefrom.

It is another object of the present invention to provide a support device which can be used either freestanding, attached to an infusion pole, or enclosed in a carrying case.

It is another object of the present invention to provide a support device which can signal the pump of a fluid delivery system which allows the pump to modify its operation depending on whether or not it is intended to be used in an ambulatory or non-ambulatory manner.

These and other objects and advantages of the present invention are realized in a specific preferred embodiment thereof, disclosed herein for purposes of example and not by way of limitation, which comprises a support device formed of a rigid body having a compartment for receiving and locking a standard infusion pump in place therein, and another, a generically-shaped compartment, for receiving and retaining a container of a fluid delivery set in a fixed position relative to the pump. The support device also includes an elongated channel extending around a substantial portion of the perimeter of the rigid body into which the tubing of the fluid delivery set can be inserted. The elongate channel is designed to approximately match the length of the tubing included on a "standard" fluid delivery set between the container and the pump to protect the tubing against kinking or occlusion along its entire length. The rigid body also includes straps, brackets, and clamps which are strategically positioned to provide maximum support for any one of several types of containers, such as soft bags, glass bottles, blow molded plastic bottles, burettes, etc.

The support device also includes a sensed means such as a magnet embedded in the pump housing which can signal a sensor such as a magnetic field sensor which can detect the sensed means when the pump is properly mounted within the pump compartment of the device. When the sensor detects the magnet, the input from the sensor to the pump causes the pump to select a modified control program which adjusts the operation of the motor within the pump to compensate for variations in fluid pressure within the fluid delivery set caused by ambulatory use of the device.

The support device is preferably designed to be insertable into a carrying case for ambulatory use. However, the rigid body also includes a base which can be used to support the entire fluid delivery system in a free standing manner on a horizontal surface, and which may include an extendable leg to increase the stability thereof during such use. Alternatively, the rigid body may include a strap which allows it to be suspended from a standard infusion pole.

These and other objects and advantages of the present invention will become apparent from the following more detailed description, when taken in conjunction with the accompanying drawings in which like elements are identified with like numerals throughout.

DETAILED DESCRIPTION OF THE PREFERRED EMBODIMENTS

Figure 1A:
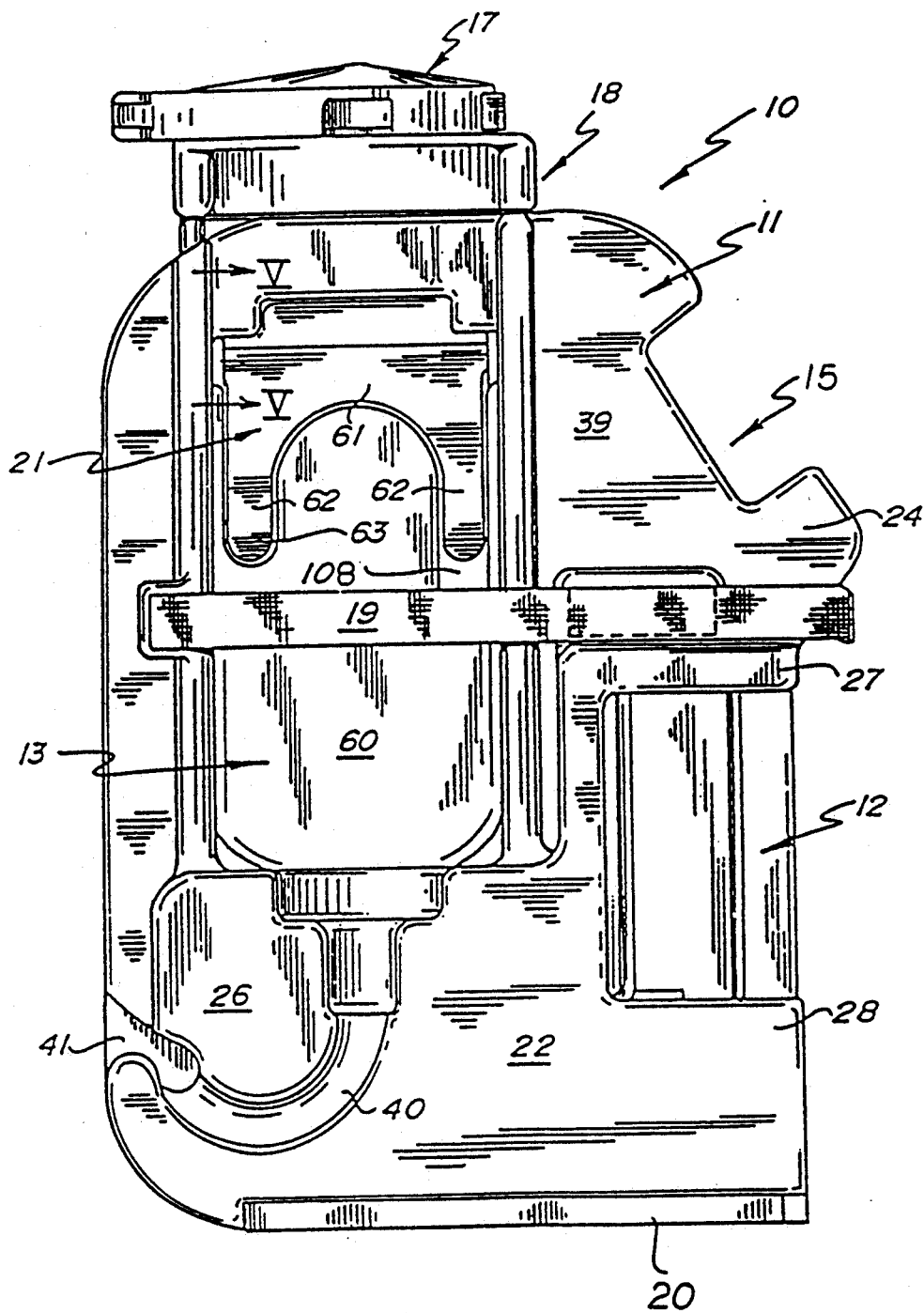
FIG. 1(a) is a front view of a support device made in accordance with the principals of the present invention.

As shown in the exemplary drawings for the purposes of illustration, an embodiment of a support device made in accordance with the principles of the present invention, referred to generally by the reference numeral 10, is provided for convenient ambulatory support of a standard (non-ambulatory type) fluid set and infusion pump of a fluid delivery system.

Figure 1B:
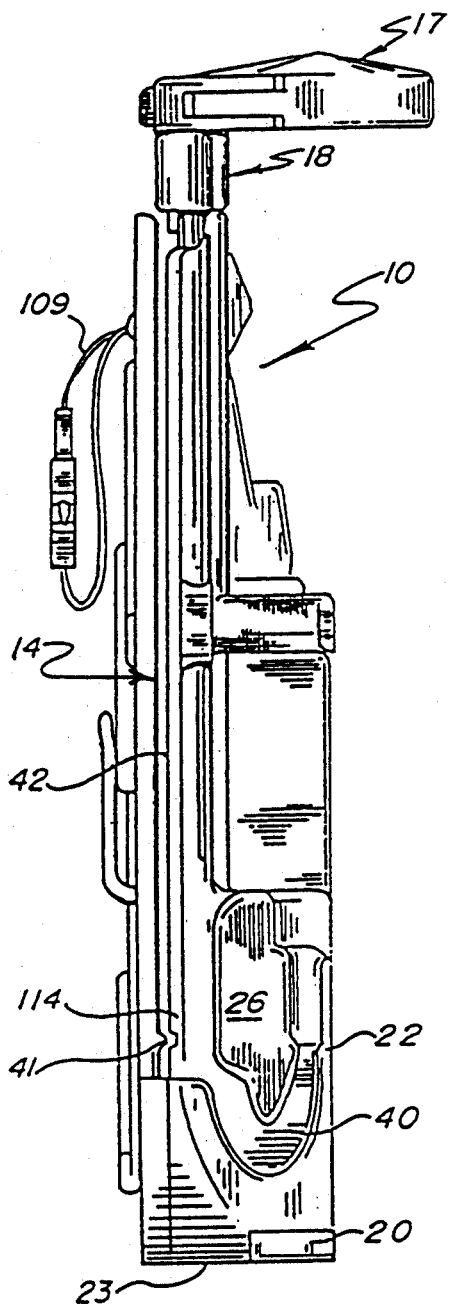
FIG. 1(b) is a left side view of the support device of FIG. 1(a)

More specifically, as shown in FIGS. 1(a)-(d), the support device 10 includes a generally rectangular rigid body 11 which is preferably formed of a rigid plastic or other lightweight material such as wood, metal alloy, etc. Referring momentarily to FIGS. 2(a)-(c) in conjunction with FIGS. 1(a)-(d), the body 11 is adapted to receive and retain a fluid delivery set 16 and an infusion pump 30 of a fluid delivery system. Specifically, the body 11 forms a pump compartment 12 adapted to receive the standard infusion pump 30, a container compartment 13 adapted to partially receive a container 47 from the standard fluid set 16, a tube channel 14 adapted to receive the tube 98 of the standard fluid set 16, and a valve compartment 15 adapted to receive a pinch valve 99 located on the tube 98 of the fluid set 16.

The support device 10 also includes a plurality of fastening elements which are adapted for use in securing the fluid delivery system to the rigid support body 11 during use. These elements include a lid clamp 17 which is permanently affixed to a lid clamp extension 18, a securing strap 19, a saddle bracket 21 which is secured in a flush mount position in the bottom 60 of container compartment 13, and a pump locking mechanism 25 (best shown in FIG. 1(c) and FIG. 3) formed as a part of the base 23 of the body 11.

The body 11 is also integrally formed with an elevated section 22 forms a part of the pump compartment 12 and cooperates with a similarly elevated section 26 to form part of the tube path 40.

An extendable leg 20 may be located below elevated section 22 so as to be flush therewith when in its retracted position, and to be perpendicular therewith and parallel to base 23 when in its extended position.

The body 11 is preferably formed by a vacuum forming process well known in the prior art, which includes vacuum forming a front portion 39 separate and apart from a back portion 45, and then permanently interconnecting the portions to complete the formation of the rigid body 11 in a well known manner. Alternatively, a reaction injection or other injection molding technology may be used to form the body 11.

Turning now to a more detailed description of each main inventive feature of the device 10, the pump compartment 12 is formed of a generally C-shaped cavity including upper and lower U-shaped channels 27 and 28, respectively, which are sized to allow the pump 30 to slide into the compartment 12 until it makes contact with the vertical abutment surface 29. The upper U-shaped channel 27 is formed contiguously with the raised surface 22 of the front portion 39 and the back portion 45, with the end of the tube channel 14 being located adjacent thereto and formed from the juncture of the front and back portions 39 and 45 as will be explained in more detail below. The lower U-shaped channel 28 is formed contiguously with the raised surface 22 of the front portion 39, the back portion 45, and the base 23.

As shown in FIG. 2(a), the upper channel 27 of the pump compartment 12 preferably includes a sensed member 86 therein. The sensed member 86 is preferably positioned so that it will be located immediately adjacent to the top surface of the pump 30 when the pump 30 is received in the pump compartment 12 of the support device 11. A preferred form of the sensed member 86 is a magnet such as is more specifically described in co-pending U.S. patent application Ser. No. 774,014 entitled "Peristaltic Infusion Device with Backpack Sensor", filed Oct. 8, 1991, which is incorporated herein by reference.

The pump 30 includes a sensor member 87 positioned within the top inner surface of the pump 30. The sensing member 87 is preferably a three pin digital magnetoresistive sensor such as described more specifically in the co-pending U.S. patent application Ser. No. 774,014 which has been incorporated herein by reference. When the pump 30 senses the presence of sensed member 86, it automatically changes its mode of operation from non-ambulatory use to ambulatory use as is also specifically described in the co-pending U.S. application Ser. No. 774,014.

Figure 1C:
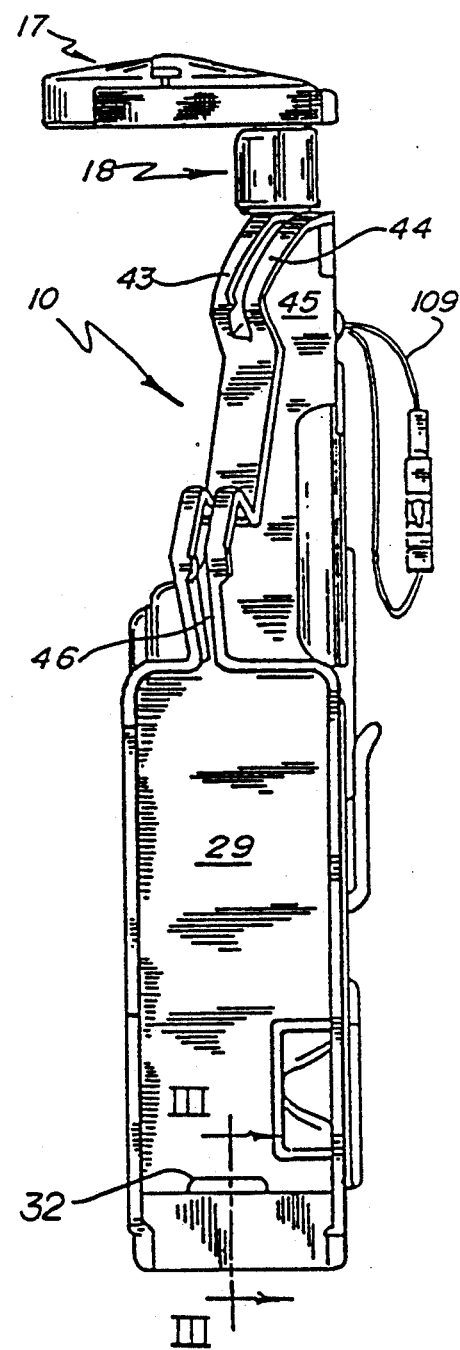
FIG. 1(c) is a right side view of the support device of FIG. 1(a)
Figure 2A:
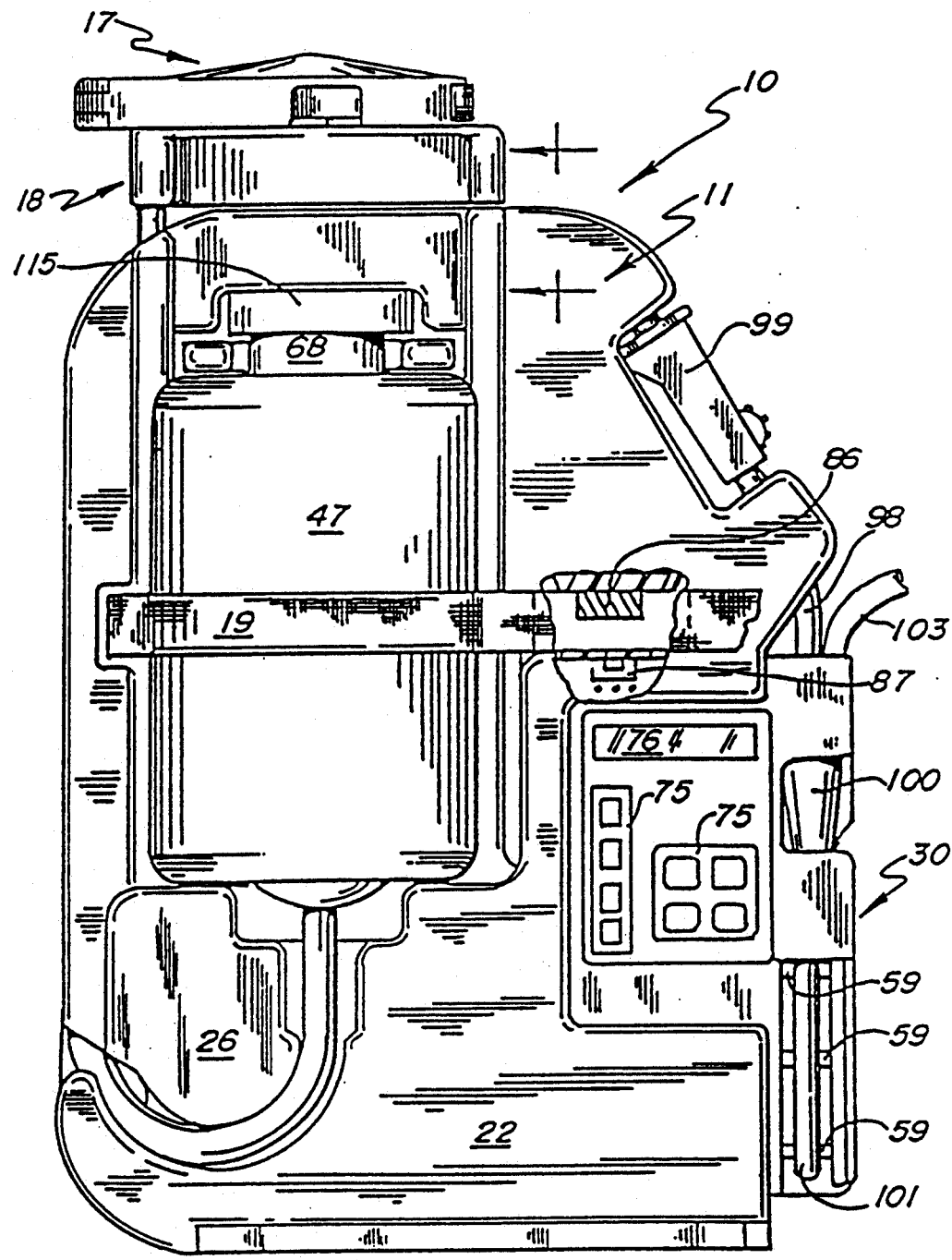
FIG. 2(a) is a front view of the support device as shown in FIG. 1(a)-(d), including a pump and a fluid infusion set with a rigid plastic bottle attached thereto for operation.
Figure 2B:
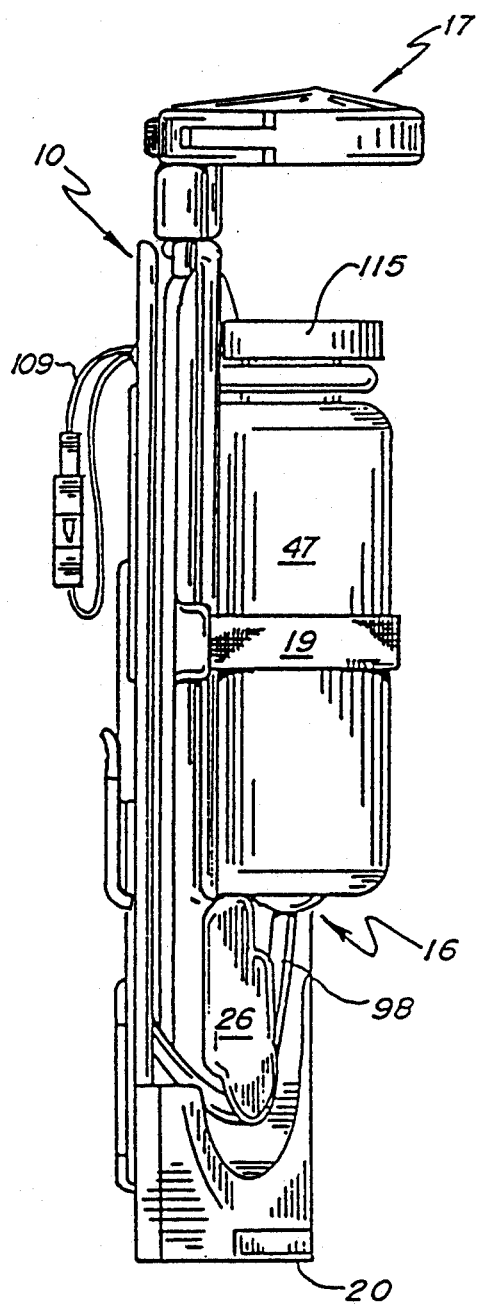
FIG. 2(b) is a right side view of the support device and attached fluid delivery set as shown in FIG. 2(a)
Figure 2C:
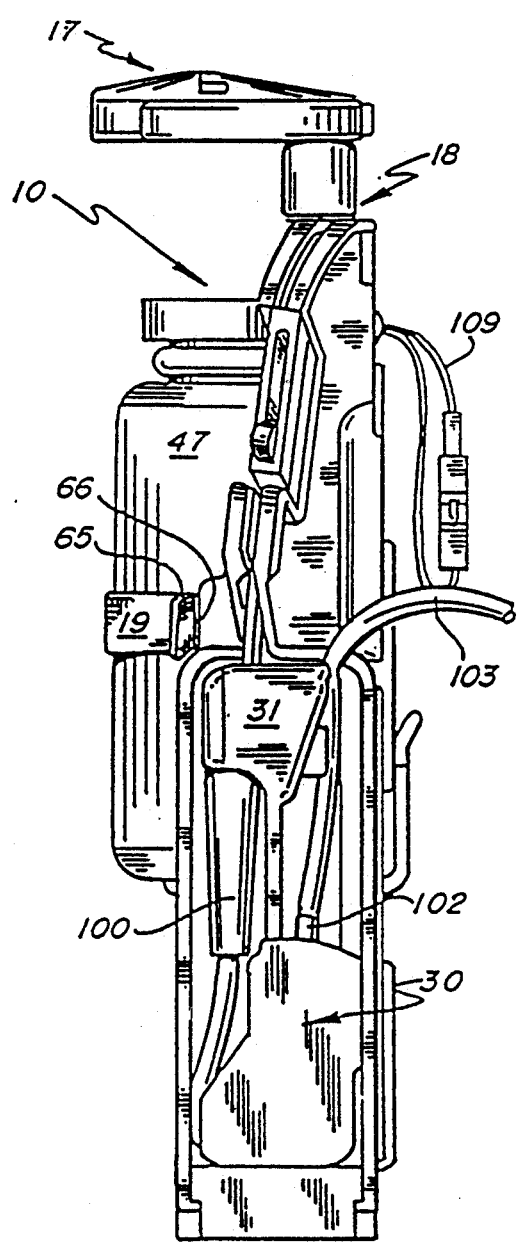
FIG. 2(c) is a right side view of the support device and attached pump and fluid delivery set as shown in FIG. 2(a)
Figure 3:
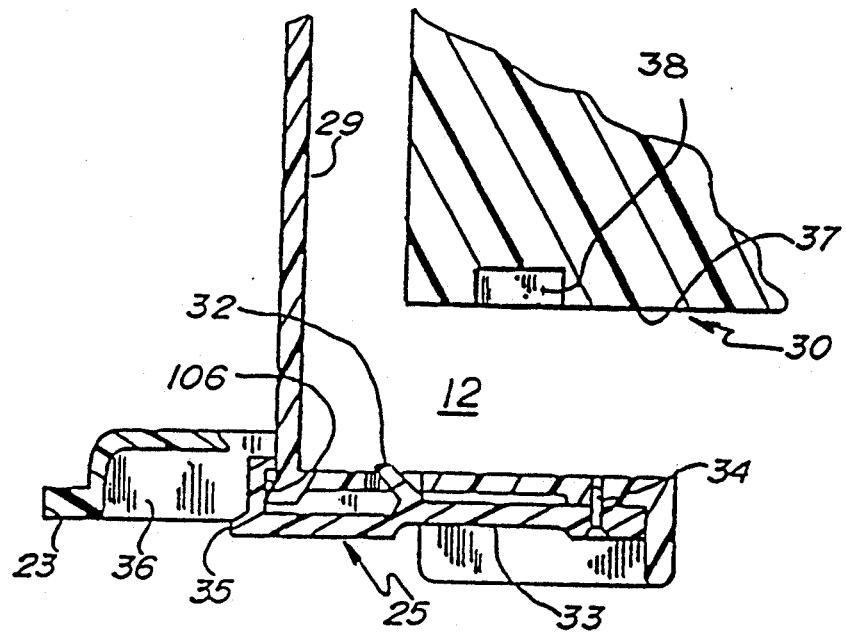
FIG. 3 is a cross-sectional view taken along line III—III of FIG. 1(c) showing a preferred embodiment of the pump locking mechanism of the present invention.
Figure 4A:
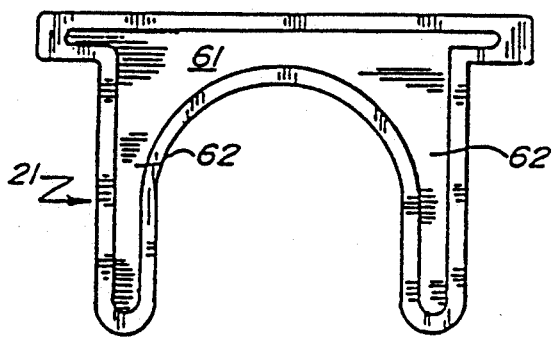
FIGS. 4(a)-(d) show a preferred embodiment of the saddle bracket of the present invention.
Figure 4B:
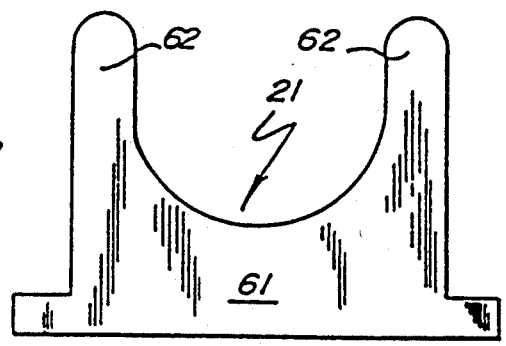
Figure 4C:
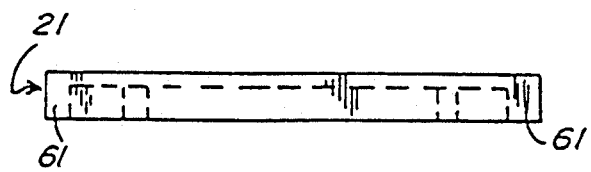
Figure 4D:

As best shown in FIG. 1(c) and FIG. 3, the pump locking mechanism 25 includes an upwardly extending locking pin 32 which protrudes into the pump compartment 12. The pin 32 is integrally formed with a lever arm 33 which in turn is connected to the base 23. It is intended that the arm 33 be somewhat flexible and may be a separate component affixed to the base 23 (as shown by screw 34) or may be integrally molded therewith. The opposite end of the lever arm 33, adjacent lock pin 32, includes a release tab 35 which can be accessed through base opening 36 by a users finger in order to move the lock pin 32 into and out of locking position within compartment 12. A stop member 106 is positioned to engage with release tab 35 when the lock pin 32 is moved out of locking position in order to prevent over flextion of the lever arm 33.

As best shown in FIG. 3, the bottom surface 37 of the pump 30 preferably includes a detent 38 which is sized and positioned so as to allow lock pin 32 to snap thereinto when the pump 30 is properly inserted within the pump compartment 12. Positioning of the pump 30 within pump compartment 12 is accomplished by sliding the pump 30 into the upper and lower U-shaped channels 27 and 28. While the pump 30 is moving into the pump compartment 12, the bottom surface 37 thereof initially pushes lock pin 32 in a downward direction until the detent 38 becomes positioned thereover (as the pump 30 abuts vertical wall 29), at which point the locking pin 32 snaps into position into the detent 38. The locking pin 32 then holds the pump within the pump compartment 12 until such time as the user pulls release tab 35 downwardly to withdraw lock pin 32 from the detent 38 and slides the pump 30 out of the pump compartment 12.

Turning now to FIGS. 2(a)-(c), the support device 10 of the present invention is shown to be adapted to receive and secure a rigid blow molded plastic bottle type container 47 commonly used with a standard fluid delivery set 16. As can be seen in FIG. 1(a), the container compartment 13 is recessed below front surface 39 of the body 11, and shaped to receive a portion of the bottle 47 in a preferred position relative to the pump 30.

The saddle bracket 21 is located within compartment 13 and flush mounted with the bottom 60 thereof so as to be out of the way when not in use. The bracket 21 includes a cross bar 61 and a pair of bracket arms 62 which extend perpendicularly therefrom and which are spaced apart from each other a distance slightly greater than the diameter of a standard feeding bottle (such as the rigid plastic bottle 47). The bracket 21 can remain flush mounted within bottom 60 of the container compartment when not in use, or can be rotated 90 degrees to cause the bracket arm 62 to extend perpendicularly from bottom 60 of the container compartment 13 and fit around the neck 68 of the bottle 47 to aid in maintaining it in its proper position during use. The saddle bracket 21 can be used in a similar manner to maintain the neck of a burette or other type of fluid container during use. Detailed explanation of other fluid containers which can be supported by saddle bracket 21 can be found in the parent co-pending U.S. patent application Ser. No. 679,886, now U.S. Pat. No. 4,170,817 issued Dec. 15, 1992 which is incorporated herein by reference.

The saddle bracket 21 rests within a cavity 63 in the bottom 60 of the container compartment 13. The cross bar 61 extends beyond the bracket arms 62 to pass into bracket arm mounting holes 64. In use, the saddle bracket 21 is lifted into its upright position by pulling bracket arm 62 upwardly from the cavity 63. This is most easily accomplished by inserting a finger into the cavity extension 108 and leveraging the arm 62 slightly out of the cavity 63. Bracket arm 62 can then be rotated until the arm 62 is in a perpendicular position by gripping the arm 62 from the container compartment 13 and rotating upwardly.

Figure 5:
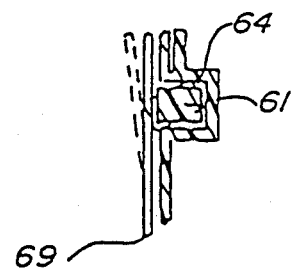
FIG. 5 is a cross-sectional view taken along line V—V of FIG. 1(a) showing the attachment of the saddle bracket to the support device of the present invention.

As best shown in FIG. 5, the cross bar 61 and the bracket arm mounting hole 64 are preferably formed into square cross-sectional shapes with a deflectable wall 69 which allows a slight resilient deformation of the mounting hole 64 as the cross bar is rotated therein. Such a design causes the arms 62 of the bracket 21 to be biased into a flush position with bottom 60 of the container compartment 13 until they are rotated approximately forty-five degrees at which point the cross bar 61 is biased to rotate to a perpendicular position where it is again properly oriented within mounting hole 64. Such a mounting design is commonly referred to as a "snap up" and/or "snap down" type mounting.

If desired for additional support of a container placed in container compartment 13, a strap 19 can be located on the front surface 39 of the body 11. The strap 19 is preferably positioned adjacent the container compartment 13 and of a sufficient length to cross over a container placed in container compartment 13 and be attached to the upper U-shaped channel 27 of the pump compartment 12. The attachment may be made in any convenient manner such as by hook and pile fasteners 65 and 66, respectively.

Figure 6A:
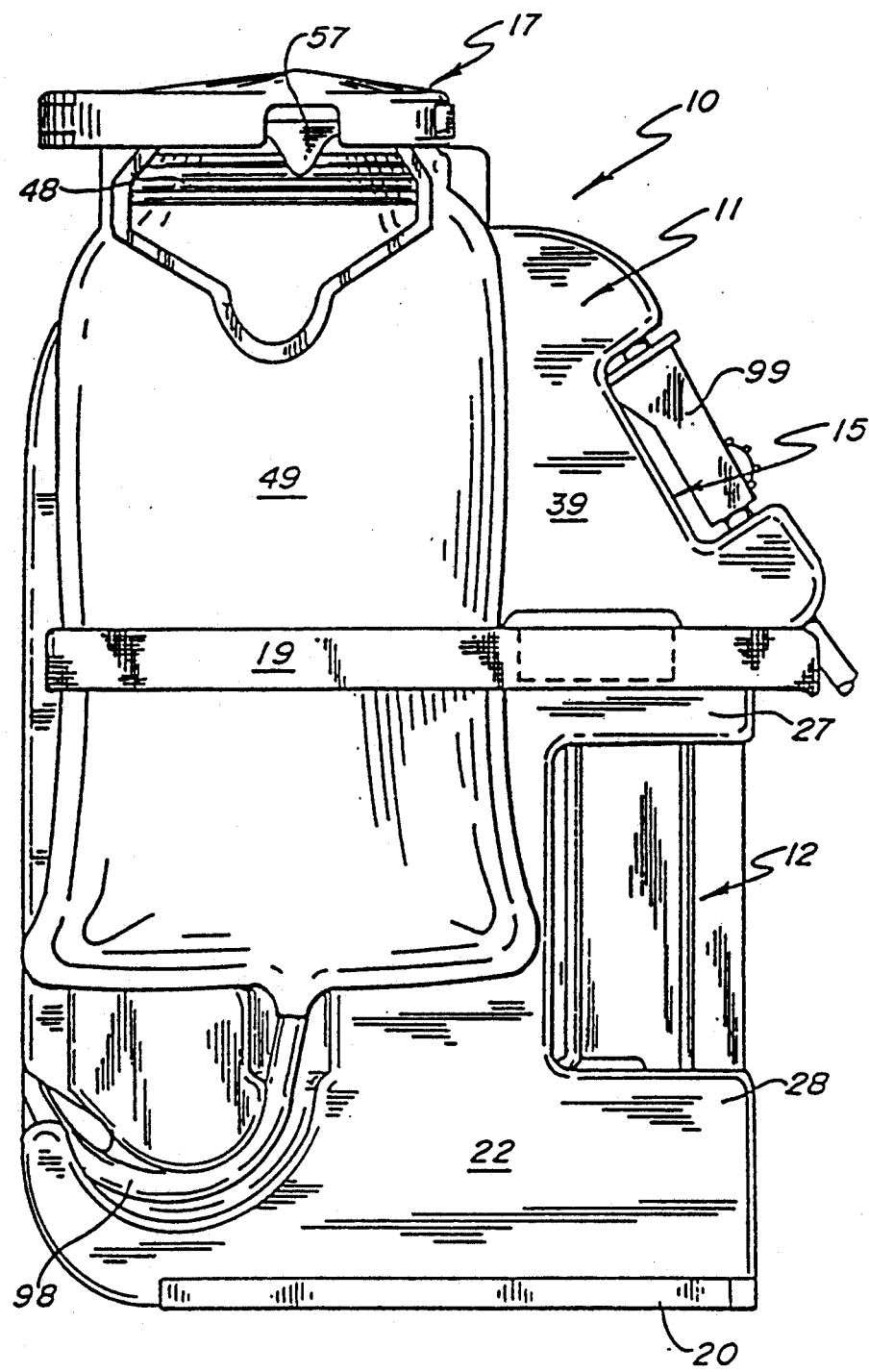
FIGS. 6(a)-(c) show the support device of the present invention as shown in FIGS. 1(a)-(c) respectively, with a fluid delivery set having a flexible bag-type fluid container attached thereto for operation.
Figures 6B, 6C:
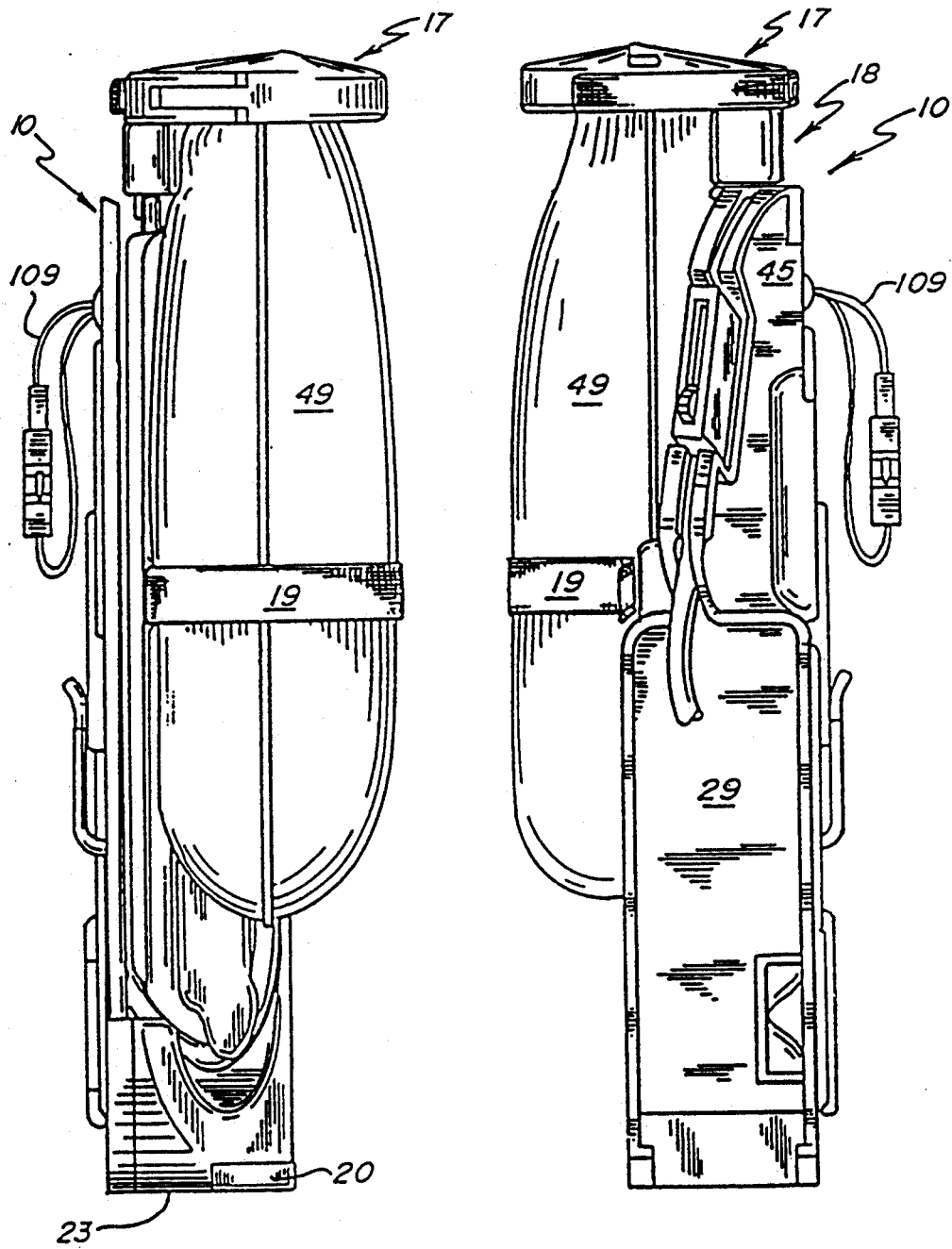
Figure 7A:
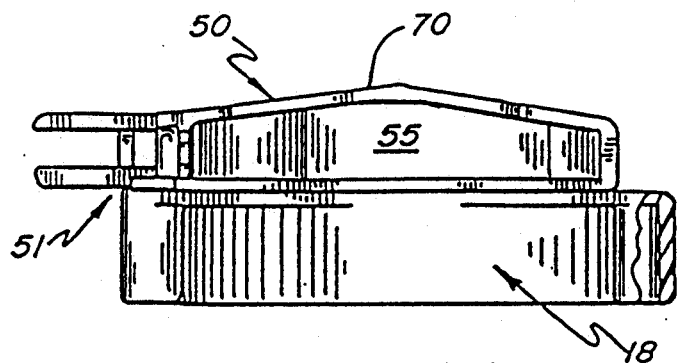
FIGS. 7(a)-(b) show a preferred embodiment of the inner clamp jaw of the lid clamp of the present invention.
Figure 7B:
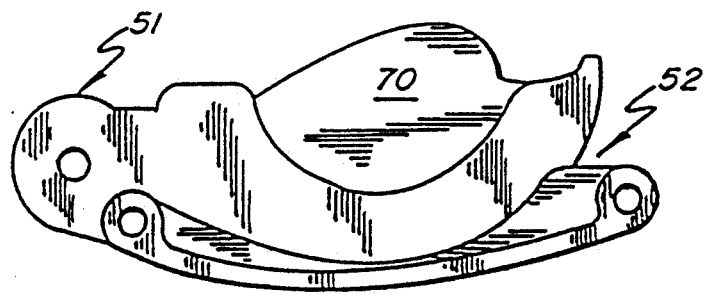
Figure 8A:
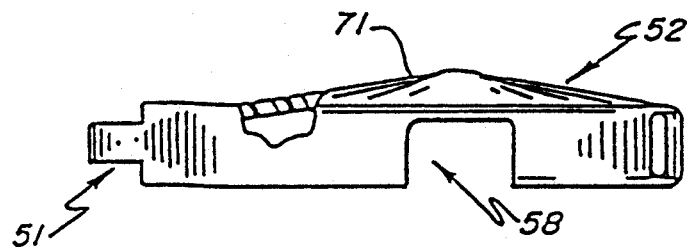
FIGS. 8(a)-(b) show a preferred embodiment of the outer clamp jaw of the lid clamp of the present invention.
Figure 8B:
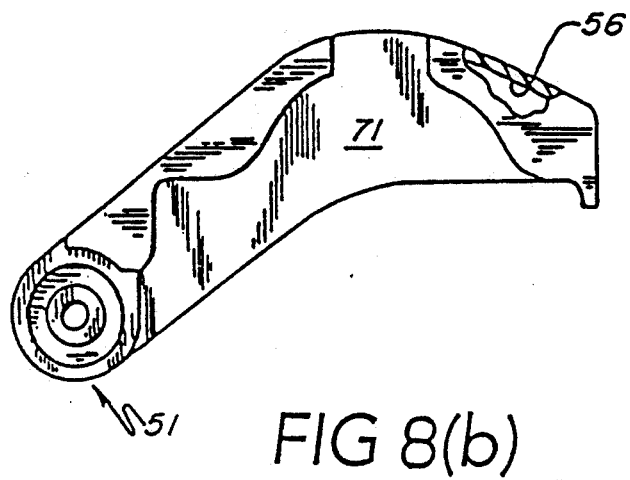

As best seen in FIGS. 6(a)-(c), the device 10 is also adaptable to receive a fluid set which includes a soft flexible fluid bag 49. The compartment 13 operates in conjunction with lid clamp 17 to hold the bag 49 in place. The lid clamp 17 includes a inner jaw 50 permanently attached to a lid clamp extension 18, and attached through hinge 51 to an outer jaw 52. A fastener, such as strap 107 including the pile portion 53 of a hook and pile type fastener, is attached to jaw 52, with the hook portion 54 of the fastener attached to jaw 50. The strap 107 allows the clamp 17 to be securely fixed in a closed position when the lid 48 of the soft bag 49 is located therein. When in the closed position, the jaws 50 and 52 of the clamp 17 form a circular opening which hold the mouth and lid 48 of the bag 49 in place on the support device 10.

As shown in FIGS. 7(a)-(b) and FIGS. 8(a)-(b), circular opening of the inner clamp jaw 50 forms an inner lip channel 55, and similarly, the outer clamp jaw 52 forms an outer lip channel 56 which receive the circumferential edges of mouth and lid 48 of the bag 49. Also, (see FIG. 6(a)) since the lid 48 generally includes an opening tab 57 thereon, the outer clamp jaw 52 is formed with a tab opening 58 through which the tab 57 can extend when the clamp 17 is closed about the lid 48.

Figure 9:
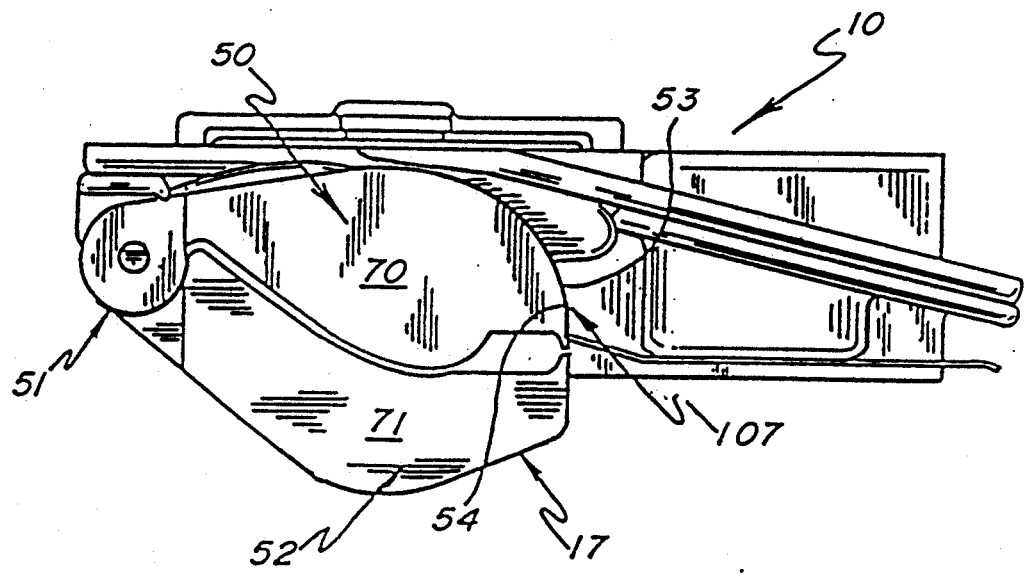
FIG. 9 is a top view of the support device of the present invention as shown in FIG. 1(a)

As shown in FIG. 9, the jaw members 50 and 52 include convex plate extensions 70 and 71 respectively which together form a generally dome-shaped surface which can effectively accommodate a bulging shape taken on by the lid 48 in the event of sudden pressurization of the bag 49 which could occur if dropped.

The lid clamp 17 operates to secure the lid 48 of bag 49 in its proper position and allow the bag 49 to be properly located within container compartment 13. Also, and more importantly, the lid clamp 17 operates to prevent the sudden application of an external pressure from inadvertently bursting the lid 48 open during use such as may occur if the support device 10 is inadvertently dropped.

Figure 10A:
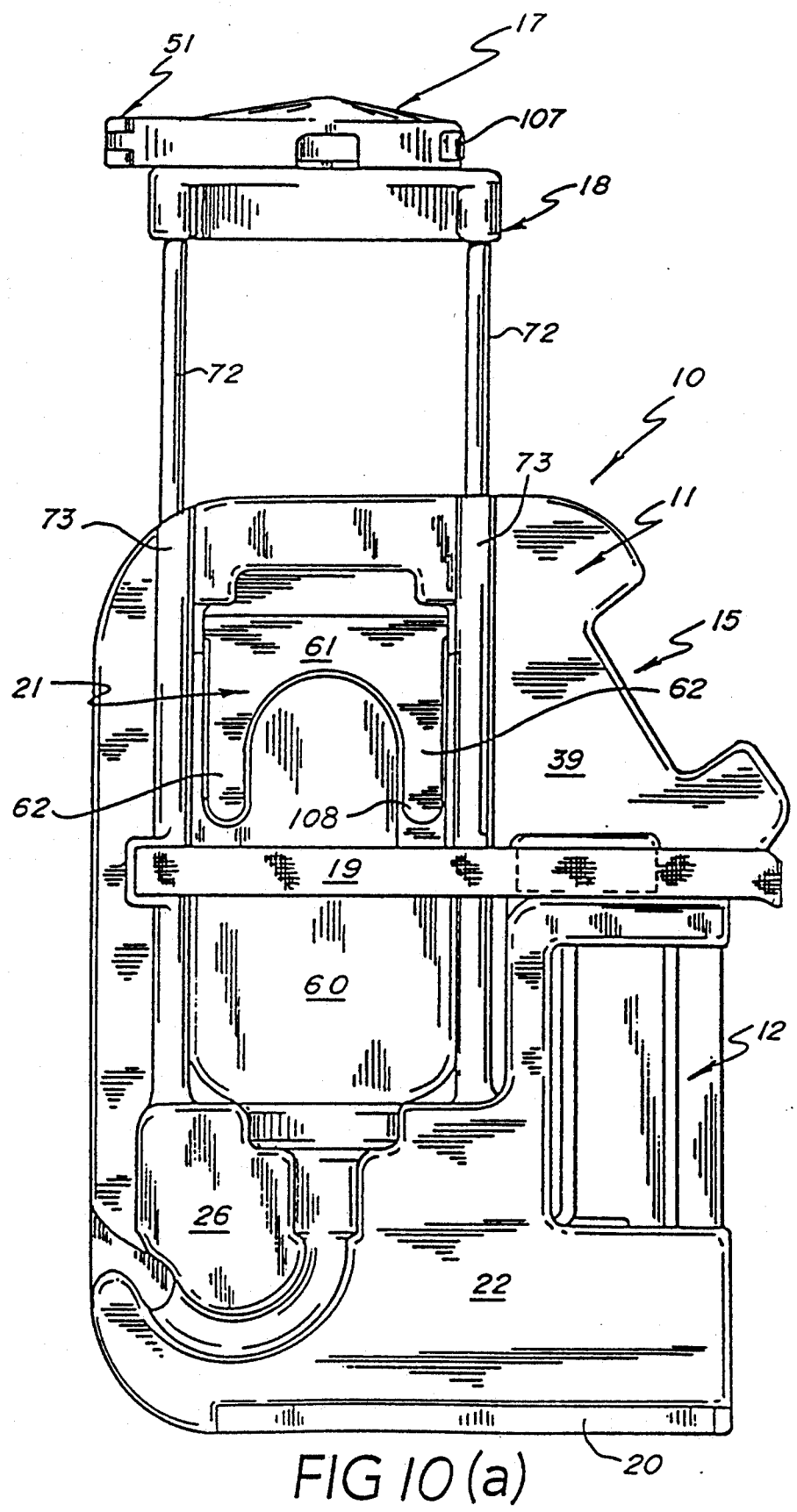
FIGS. 10(a)-(c) show a front view, left side view, and rear view respectively, of the support device of the present invention with the fluid container lid clamp thereof extended for use of the device with fluid delivery sets including large fluid containers.
Figure 10:
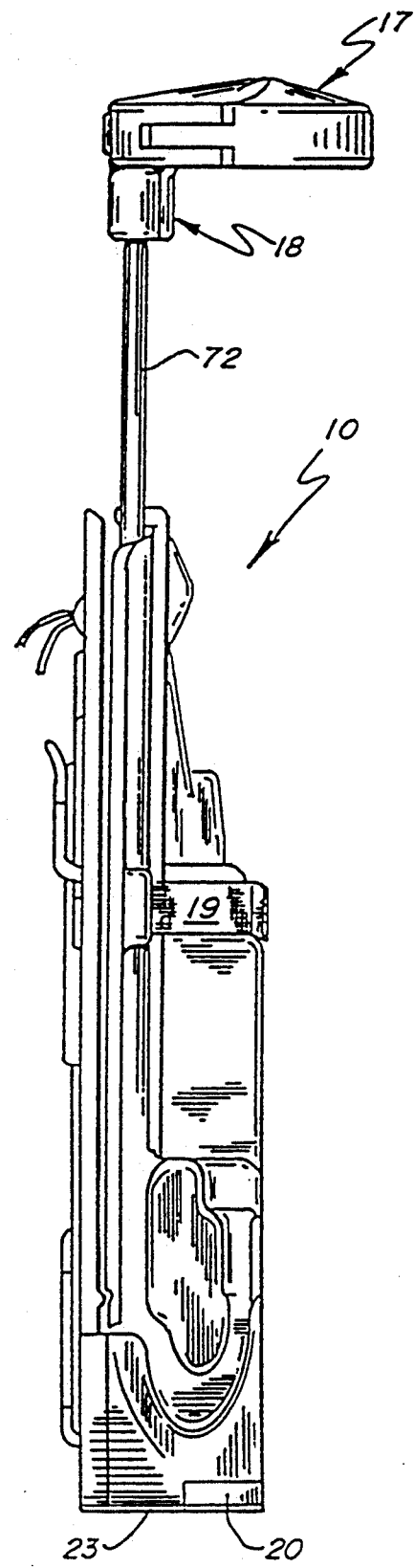

The lid clamp 17 can be positioned above container compartment 13 a sufficient distance to allow the accommodation of the desired size of bag 49. For example, as shown in FIGS. 6(a)-(c), the lid clamp extension 18 may be located directly adjacent the body 11 to allow the container compartment 13 to accept and properly position a bag 49 of standard 600 ml. volume. Alternatively, as shown in FIGS. 10(a)-(c), the lid clamp extension 18 can be moved to a predetermined position which is a sufficient distance from the body 11 to allow room in container compartment 13 to accept a bag 49 of a standard 1000 ml. volume.

The lid clamp extension 18 is mounted for movement relative to the body 11 by means of extension rods 72. The rods 72 are mounted in the front portion 39 of the body 11 through the tubular channels 73.

Figure 10C:
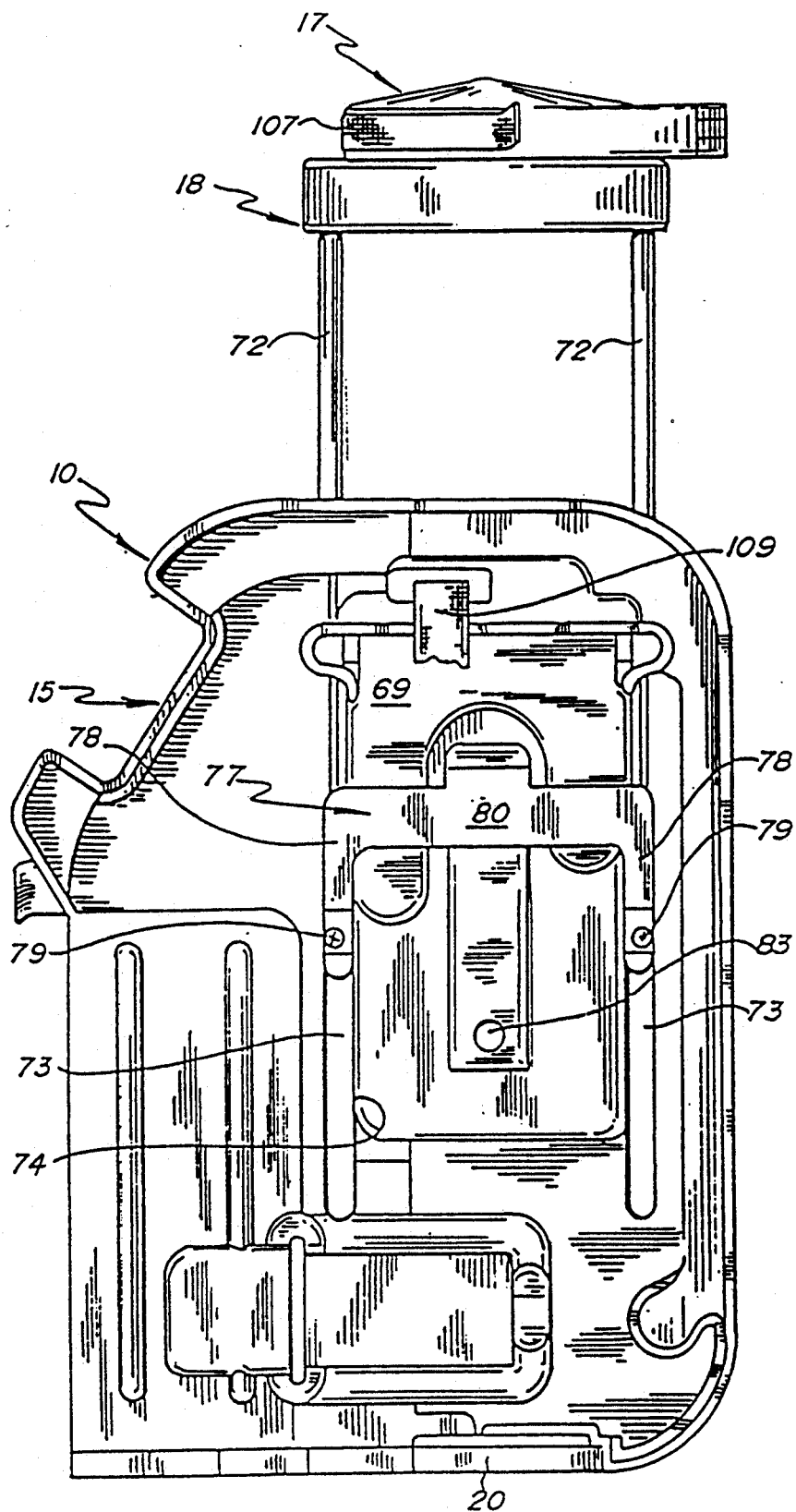
Figure 11A:
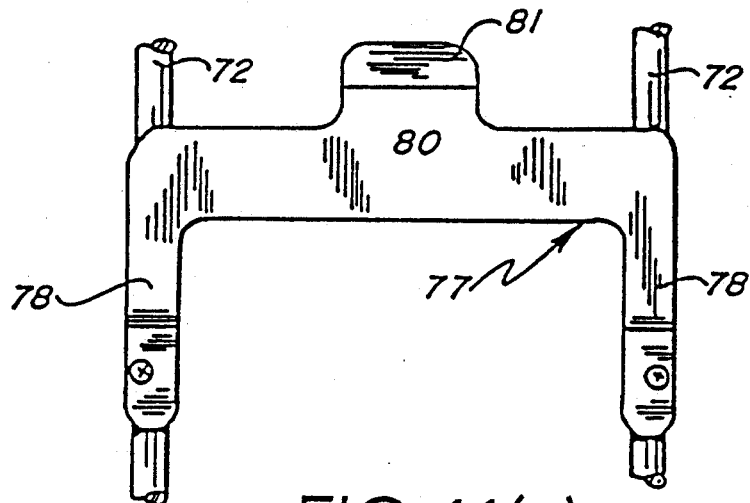
FIGS. 11(a)-(c) show a preferred embodiment of a locking mechanism for the extension clamp of the support device.
Figure 11B:
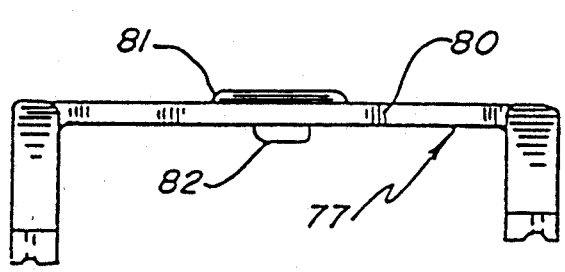
Figure 11C:
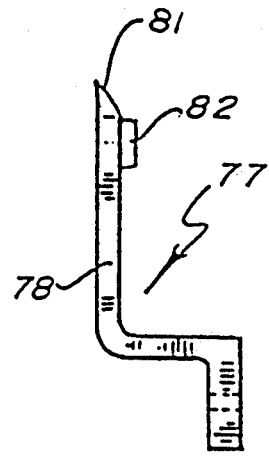

As best shown in FIG. 10(c), slots 74 extend through back portion 45 of the body 11 to expose the tubular channels 73. A U-shaped extension locking member 77, having arms 78 is attached to the bottom of each extension rod 72 such as by means of screws 79 or in any other well known manner.

As best shown in FIG. 10(c) and FIGS. 11(a)-(c), the U-shaped extension locking member 77 includes a bail portion 80 which extends between the arms 78 and includes a release tab 81 and locking pin 82 formed at a generally central location thereon.

Figure 1D:
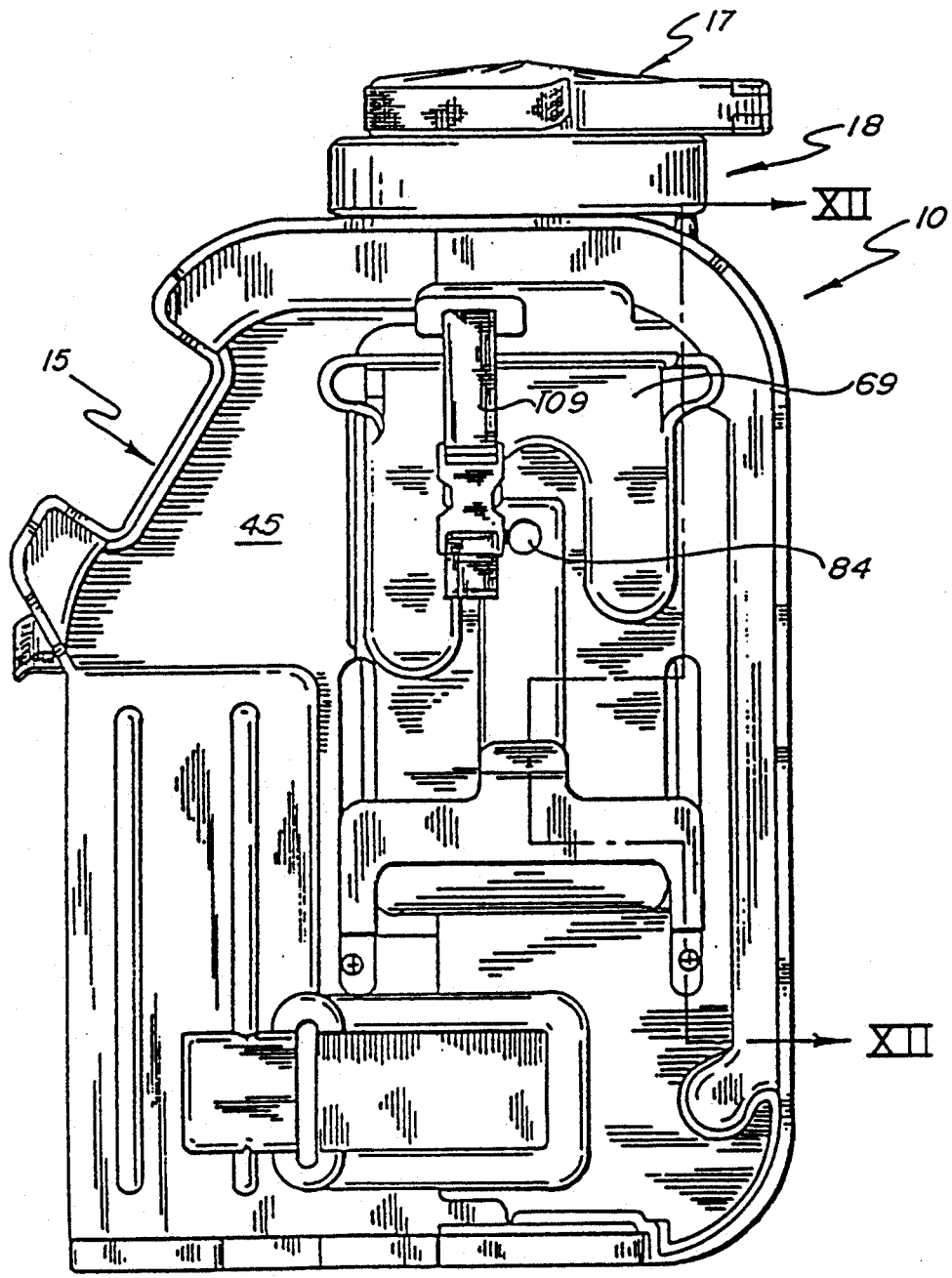
FIG. 1(d) is a rear view of the support device shown in FIG. 1(a)
Figures 12, 13:
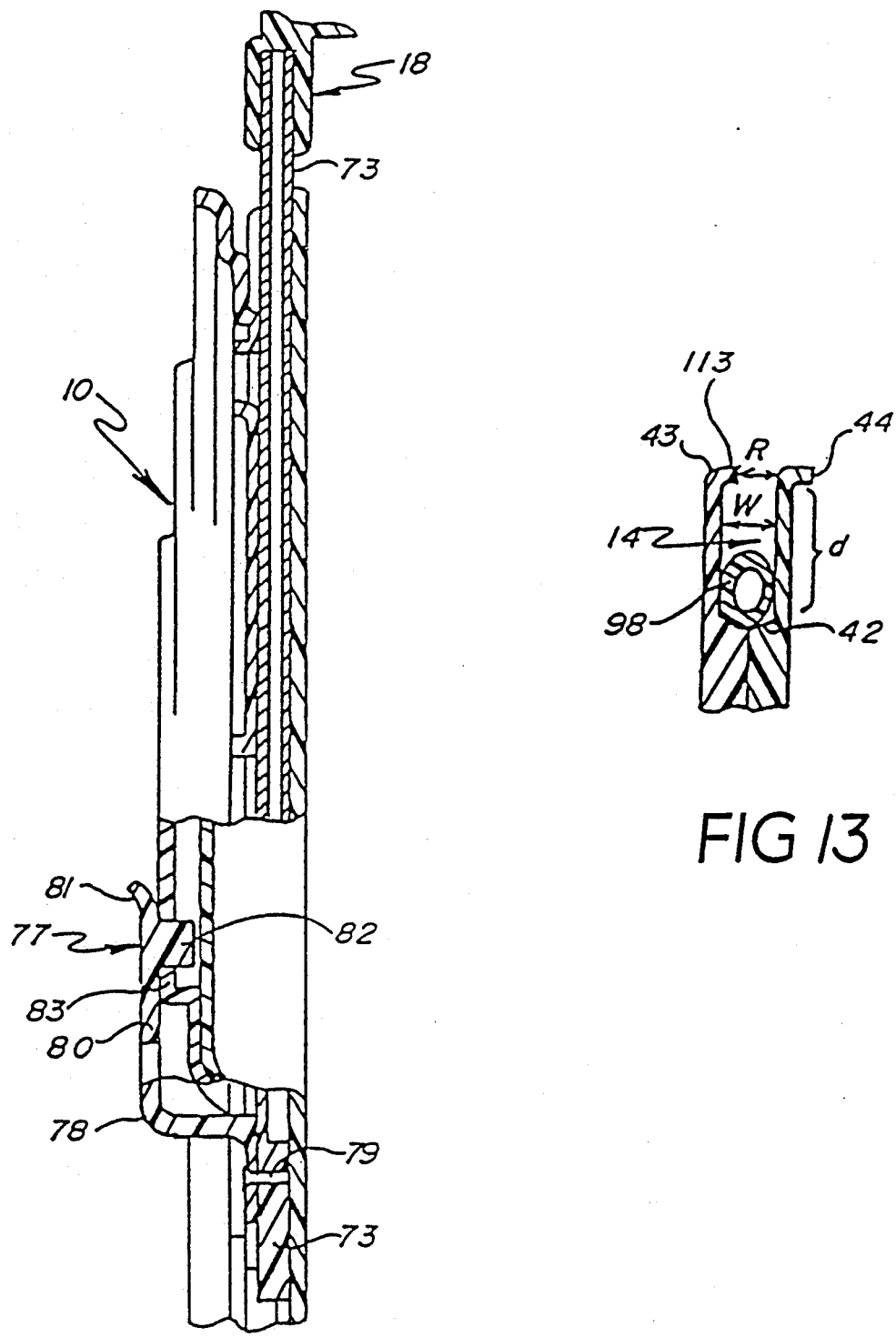
FIG. 12 is a cross-sectional view taken along line XII—XII of FIG. 1(d) showing the operation of the lid clamp locking mechanism of the support device.
FIG. 13 is a cross-sectional view taken along line XIII—XIII of FIG. 2(a) showing the tubing of a fluid delivery set located in a preferred embodiment of the tubing compartment of the support device of the present invention.

As best shown in FIG. 12, the locking member 77 is designed to allow locking pin 82 to be positioned within opening 83 in the back portion 45 of the body 11 in order to lock the lid clamp 17 in position adjacent the body 11 (see FIG. 1(d)). When it is desired to move the lid clamp 17 to an extended position away from the body 11, the release tab 81 is lifted away from the back portion 45 of the body 11 to disengage locking pin 82 from opening 83. The extension locking member 77 is then pushed in the upper direction until locking pin 82 can engage opening 84. As the extension locking member 77 is moved in an upward direction, the arms 78 thereof attached to the extension rod 72 force the extension rod 72 to slide upwardly in slots 74 to force the extension rods 72 to slide in the upper direction in the tubular channel 73. Once the locking pin 82 is engaged in opening 84, the lid clamp 17 is properly located in its extended position (see FIG. 10(c)).

As best shown in FIGS. 1(a)-(c), the tube channel 14 of the support device 10 extends around approximately two thirds of the circumference of the body 11. The tube channel 14 is generally U-shaped in cross-section and includes a base 42, a front wall 43, and a back wall 44.

The tube channel 14 is essentially a channel between the front and back portions 39 and 45, respectively, of the body 11, and extends from entrance opening 41 across the top and partially down the opposite side of body 11 to exit opening 46. Slightly above exit opening 46, the channel 14 is interrupted by a pinch clamp compartment 15 which is sized to receive the standard type pinch clamp 99 commonly attached to the tubing 98 of a fluid delivery set 16. The pinch clamp compartment 15 is formed by a cut out section of the body 11, and is sufficiently large to allow the pinch clamp 99 (see FIG. 2(a)) to rest therein when the tubing 98 is located in the tube channel 14.

As can be seen in FIG. 13, the channel 14 is designed to allow accommodation of the tubing of the fluid set 16 even though slight variations in length thereof may occur. This is because the channel 14 is of sufficient depth (d) to allow some "snaking" of the tube within the channel 14 if necessary to accommodate its entire length.

Further, the channel 14 is also designed to retain the tubing therein once place, even though some "snaking" may occur. Specifically, the channel 14 is generally of a width (w) which is slightly larger than the diameter of the tube 98. However, at the top of the channel 14, the width (R) is restricted to a dimension less than the diameter of the tube 98. The restriction is in the form of a lip 113 which ensures that the tubing 98 stays within the channel 14. Without the pressure of the lip 113, the tube 98 would have the mechanical inclination to bow outwardly and at least partially escape the channel 14 at various locations around the body 11.

Due to the presence of the lip 113, it is advantageous to form a tapper 114 at the inlet opening 41 of the channel 14 for ease of beginning the insertion of the tube 98 into the channel 14.

Because of the restricted width (R) of the channel 14 at the lip 113, the tube 98 becomes resiliently deformed into an oval cross-sectional shape while passing into the channel 14. Once the tube 98 is forced entirely within the channel 14, it will return to its circular cross-sectional shape and will thereafter be retained within the channel 14 until forcibly withdrawn therefrom.

Located below container compartment 13 are the elevated sections 22 and 26 of the body 11 which are oriented to form a tube path 40 for passing a tube from a container placed in container compartment 13 to the entrance 41 of the tube channel 14.

As best illustrated in FIG. 1(a) and (c), the forward sloping section 24 of the body 11 causes the exit opening 46 of the tube channel 14 to be positioned somewhat centrally over the pump compartment 12. This is advantageous in that it allows the tubing of the fluid delivery set to pass from channel 14 at exit opening 46 in the proper position for reception into the hinged pump arm 31 of the pump 30.

The support device 10 is adapted to be used with the pump 30 and fluid delivery set 16 in a variety of environments. For example, body 11 of the support device 10 may be mounted to a standard infusion pole for use with bed ridden or ambulatory patients by means of mounting hole 109. Alternatively, the device 10 may be placed into a carrying case and strapped to the patient's back for ambulatory use. Examples of carrying cases adapted for use with device 10 are illustrated and described in co-pending parent U.S. application Ser. No. 679,886, incorporated herein by reference. Further, the device 10 may be placed on its base 23 on a level surface such as a table or the like without the need for any other mounting aid. In such an instance, the support leg 20 located in the base 23 of the device 10 may be used to add stability to the base 23 during use.

Figure 14:
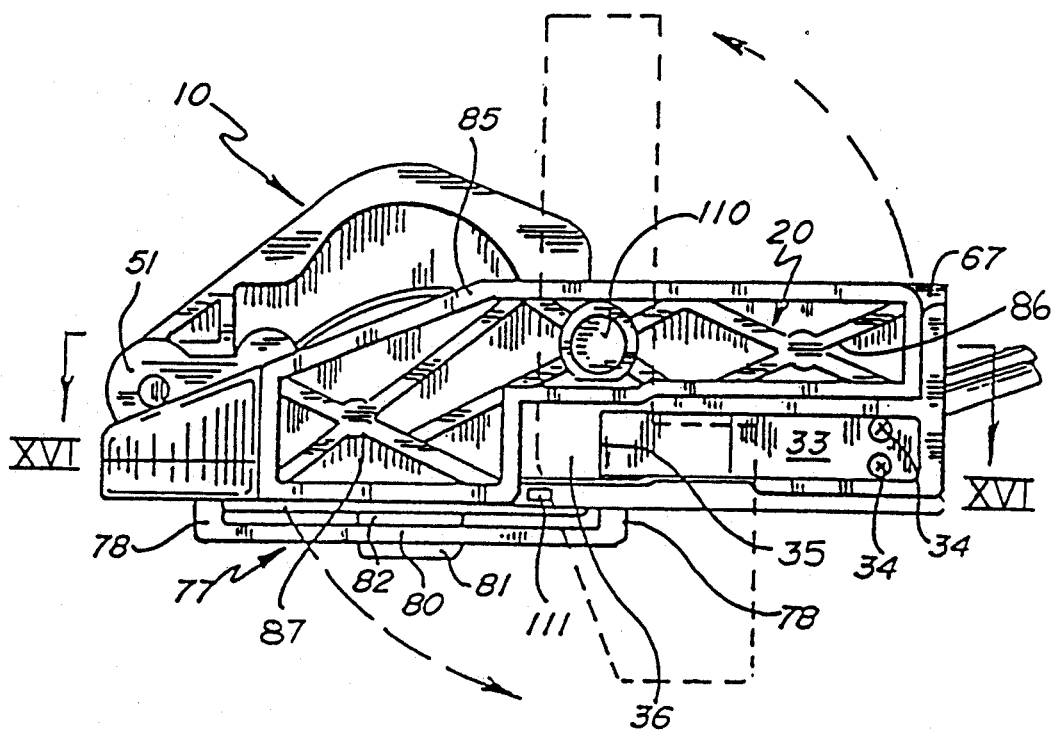
FIG. 14 is a bottom view of the support device of the present invention as shown in FIG. 1(a)

As shown in FIG. 14, the leg 20 can be rotated to an open position parallel with the front and back portions 39 and 45 of the body 11 and flush with base 23 to prevent inadvertent tipping of the device in the forward or backward direction.

Figure 16:
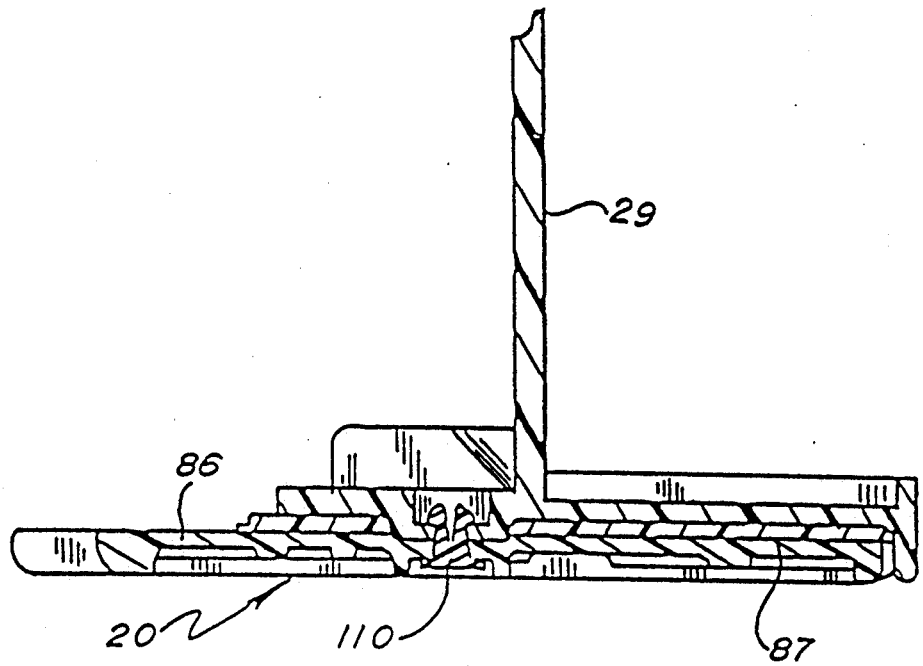
FIG. 16 is a cross-sectional view taken along lines XVI—XVI of FIG. 14 showing the support leg of the support device of the present invention.

As shown in FIGS. 14 and 16, the leg 20 is mounted on the bottom of the support device 10 in such a manner to form a substantial portion of the base 23 thereof. The leg 20 is mounted for rotation about pivot pin 110. As shown in dash lines in FIG. 14, the leg 20 can rotate approximately 90 degrees until locking edge 85 thereof passes completely beyond the locking surface 111 in which position the leg 20 is maintained due to the frictional contact between the frictional locking surface 111 and the edge portion 85. In the operation position as shown in dash lines in FIG. 14, the leg 20 includes a forward extension 86 and a backward extension 87 which are substantially perpendicular to both the height and width of the body 11, and parallel and flush with the remainder of the base 23.

Figure 15A:
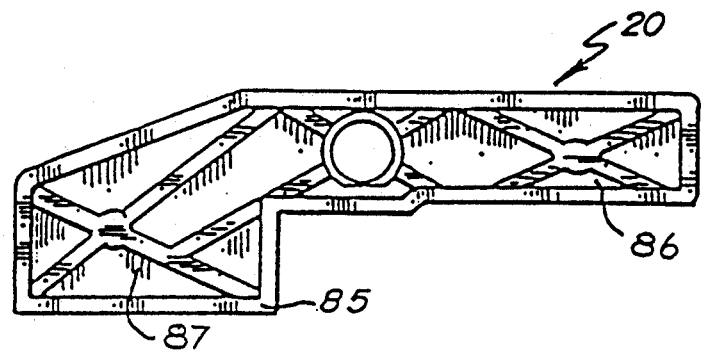
FIGS. 15(a)-(b) show a preferred embodiment of the rotatable support leg of the support device.
Figure 15B:
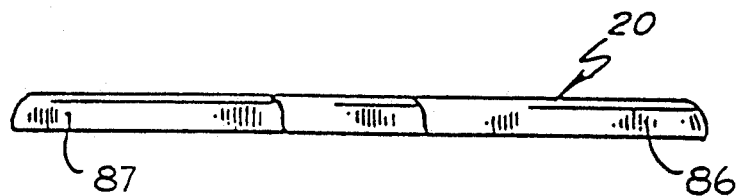

As best shown in FIGS. 15(a)-(b), the leg member 20 is a generally elongated flat member which is shaped to fit completely within the perimeter dimensions of the base 23 of the support device 10 when in its retracted position.

As best shown in FIG. 2(a), the fluid delivery set 16 includes a container such as the plastic bottle 47, with a standard length of tubing 98 extending from the bottom thereof. The tubing 98 includes a pinch valve 99 thereon and a drip chamber 100 attached at its distal end. The drip chamber 100 is also attached to an extensible, relatively thin-walled pump roller tube 101 which is especially adapted for use with the pump 30. An extension ring 102 is attached to pump tubing 101 and functions to insure that the pump tubing 101 is properly stretched over the rollers 59 of the pump 30 when in use. Beyond extension ring 102 is an infusion tube 103 which is intended to be attached to the patient.

It is to be understood that although the present invention is described for use in conjunction with the specific fluid delivery sets 16 and a specific pump 30, any well known type fluid delivery set or infusion pump may be used with or adapted for use with the support device 10 of the present invention and remain within the intended scope and meaning of the present disclosure. Similarly, obvious adaptions to the support device 10 necessary to accommodate other well known type delivery sets and pumps are intended to fall within the scope of the present invention.

A preferred method of attachment of the fluid delivery set 16, including the rigid bottle 47, and the pump 30 to the support device 10 of the present invention is described as follows. As shown in FIGS. 2(a)-(c), the pump 30 is inserted into pump compartment 12 until it is locked in position by pump locking mechanism 25. The saddle bracket 21 is lifted to its "pop-up" position and the bottle 47 is inserted into the container compartment 13 until tubing 98 thereof can extend into the tube path 40. In this position, the bracket 21 secures the neck 68 of the bottle 47 against lateral movement. The strap 19 is then secured over the bottle 47 to prevent its escape from the compartment 13. Next, the tube 98 is grasped and forced into entrance 41 of tube channel 14 and drawn the entire length of channel 14 until pinch valve 99 is reached.

Pinch valve 99 is then adjusted along tubing 98 until it is oriented properly to be received in pinch valve compartment 15. Tubing 98 is then extended through the remainder of tubing channel 14 and allowed to extend beyond exit 46.

Once the tube 98 is properly placed, the drip chamber 100 is inserted into the opened arm 31 (not shown in the open position) of the pump 30 and pump tubing 101 is passed around the pump roller 59 until the retention ring 102 is properly positioned in a slot (not shown) within the arm 31 in such a manner as will cause the tube 101 to be stretched over the roller 59 of the pump 30 when the arm 31 is moved to its closed position. The pump arm 31 is then rotated into its closed and operating position and the infusion tube 103 is extended away from the pump arm toward the patient.

If desired, the support device may be placed on an infusion pole by inserting a hook thereof (not shown) through strap 109. Alternatively, legs 20 may be rotated to its extended position and the support device 10 may be rested on its base 23 on a horizontal surface such as a table or the like. Finally, should the patient wish to be completely ambulatory, the support device may be inserted into a carrying case with the infusion tube 103 extending out of an opening in the case to be attached to the patient.

Fluid delivery sets of the type having the flexible bag 49 are attached to the support device 10 in a manner similar to that described above with respect to the rigid bottle type fluid infusion set 16, except that the lid clamp 17 is moved to the desired extension position, and the lid 48 of the flexible bag 49 is inserted into the lid clamp 17 and securely clamped in place.

Similarly, fluid infusion sets 16 which include a burette type container can be positioned in the support device 10 in a manner similar to that described above with respect to the rigid bottle 47 in FIGS. 2(a)-(c), with the burette 59 placed between the bracket arms 62 of the saddle bracket 21.

With each type of fluid infusion set, if desired or necessary, the strap 19 may be used to secure the container and the container compartment 13. Although not shown, other standard fluid sets 16, such as spike sets, etc. can be similarly used with the support device 10 of the present invention. A more detailed description of the method of attachment of the pump 30 and various types of fluid sets 16 to the support device 10 of the present invention is found in co-pending parent U.S. patent application Ser. No. 679,886, now U.S. Pat. No. 5,170,817, issued Dec. 15, 1992 which is incorporated herein by reference.

It will be apparent from the foregoing, while particular embodiments of the invention have been illustrated and described, various modifications can be made thereto without departing from the spirit and scope of the present invention. Accordingly, it is not intended that the invention be limited, except as by the appended claims.

What is claimed is:

1. A support device for a fluid delivery system including a fluid delivery set and a pump, the fluid delivery set including a fluid container and a tube for connection to the pump, said device comprising
a body means having:
means for holding the pump,
adjustable means for holding the container, said adjustable means including means for securing at least a portion of the container in fixed position relative to said body means, and
means for preventing kinking or occlusion of the tube between the container and the pump.

2. A support device according to claim 1 wherein said adjustable means for holding the container includes a recess within a front surface of said body means, said recess including a substantially flat bottom surface against which a portion of the container rests when properly attached to said body means.

3. A support device according to claim 1 wherein said body means is formed of a rigid material.

4. A support device according to claim 3 wherein said body means maintains said means for holding the pump, adjustable means for holding the container and said means for preventing kinking or occlusion of the tube, in fixed spaced relationship relative to each other.

5. A support device according to claim 1 wherein said adjustable means includes strap means attached to said body means and operable to partially surround a container located adjacent said body means to aid in holding the container in a relatively fixed position relative to said body means.

6. A support device according to claim 1 wherein said means for securing at least a portion of the container further includes clamp means for securing the container in relatively fixed position relative to said body means.

7. A support device according to claim 6 wherein said adjustable means further includes extension means for adjusting the position of said clamp means relative to said body means.

8. A support device according to claim 7 wherein said extension means includes an extension locking member for locking said clamp means in any one of a plurality of positions relative to said body means in order to accommodate various sizes of containers.

9. A support device according to claim 8 wherein said extension locking member is attached to said clamp means by at least one extension rod.

10. A support device according to claim 9 wherein said at least one extension rod is mounted in at least one generally tubular channel formed by said body means for slidable movement relative to said body means.

11. A support device according to claim 6 wherein said clamp means secures the container by substantially surrounding a mouth and lid of the container.

12. A support device according to claim 1 further including leg means attachable to said body means and rotatable between a first position in which said leg means is located within said body means and flush with a front surface of said body means, and a second position in which said leg means is oriented substantially perpendicularly to said front portion of said body means.

13. A support device according to claim 12 wherein said leg means is a single elongated generally flat member including first and second extensions and mounted for rotation within a base of said body means,
whereby, rotation of said leg means to said second position causes said first extension to extend away from said front portion and said second extension to extend away from a back portion of said body means.

14. A support device for a fluid delivery system including a fluid delivery set and a pump, the fluid delivery set including a fluid container and a tube for connection to the pump, said device comprising
a body means having:
means for holding the pump,
adjustable means for holding the container, and
means for preventing kinking or occlusion of the tube between the container and the pump
said adjustable means for holding the container including U-shaped bracket means mounted within a recess within a front surface of said body means, said recess including a substantially flat bottom surface against which a portion of the container rests when properly attached to said body means.

15. A support device according to claim 14 wherein said U-shaped bracket means includes a spring bar member which operates to assist the U-shaped bracket means to maintain a position generally perpendicular to said substantially flat bottom surface when securing a neck and lid of the container.

16. A support device according to claim 14 wherein said adjustable means for holding the container includes a recess within a front surface of said body means, said recess including a substantially flat bottom surface against which a portion of the container rests when properly placed adjacent said body means, and a U-shaped bracket means is mounted within said flat bottom surface and is operable between a first position in which said U-shaped bracket means is flush with said flat bottom surface, and a second position in which said U-shaped bracket means is rotated approximately 90 degrees to be substantially perpendicular to said flat bottom surface.

17. A support device for a fluid delivery system including a fluid delivery set and a pump, the fluid delivery set including a fluid container and a tube for connection to the pump, said device comprising a body means having:

means for holding the pump, adjustable means for holding the container, said adjustable means including clamp means for securing the container in fixed position relative to said body means, and means for preventing kinking or occlusion of the tube between the container and the pump.

* * * * *